United States Patent [19]

Anderson et al.

[11] Patent Number: 4,829,810
[45] Date of Patent: May 16, 1989

[54] FILAMENT DRIVE CIRCUIT

[75] Inventors: Daniel A. Anderson, Greensburg; Ronald C. Wojnar, Upper Burrell Township, Westmoreland County; Mark F. A. Warchol, New Kensington, all of Pa.

[73] Assignee: Aluminum Company of America, Pittsburgh, Pa.

[21] Appl. No.: 140,749

[22] Filed: Jan. 4, 1988

[51] Int. Cl.[4] .............................................. G01N 27/18
[52] U.S. Cl. .................................... 73/27 R; 73/19; 422/96; 338/34
[58] Field of Search .......................... 73/23, 27 R, 19; 422/96, 98; 436/149; 338/34; 164/4.1; 266/78; 204/408

[56] References Cited

U.S. PATENT DOCUMENTS

| | | | |
|---|---|---|---|
| 4,222,006 | 9/1980 | Schneider | 204/408 |
| 4,454,748 | 6/1984 | Terai et al. | 73/27 R |
| 4,498,330 | 2/1985 | Hosoya | 73/27 R |
| 4,533,520 | 8/1985 | Bossart et al. | 73/27 R |
| 4,735,082 | 4/1988 | Kolloff | 73/27 R |
| 4,741,198 | 5/1988 | Farren et al. | 73/27 R |

FOREIGN PATENT DOCUMENTS 2094483 9/1982 United Kingdom ................ 436/149

Primary Examiner—Stewart J. Levy
Assistant Examiner—Michele Simons
Attorney, Agent, or Firm—Elroy Strickland

[57] ABSTRACT

An apparatus and a method is provided for determining the equilibrium of the partial pressures of two gases having different thermal conductivities. The apparatus includes a single sensor adapter to be contacted by the two gases, and heated by a flow of electrical current through the sensor. A circuit is provided for maintaining the sensor at a constant level of electrical resistance and hence at a constant temperature. The sensor, in addition, is connected as one leg of a bridge circuit, the output of which represents changes occurring in the thermal conductivity of a mixture of the gases.

2 Claims, 1 Drawing Sheet

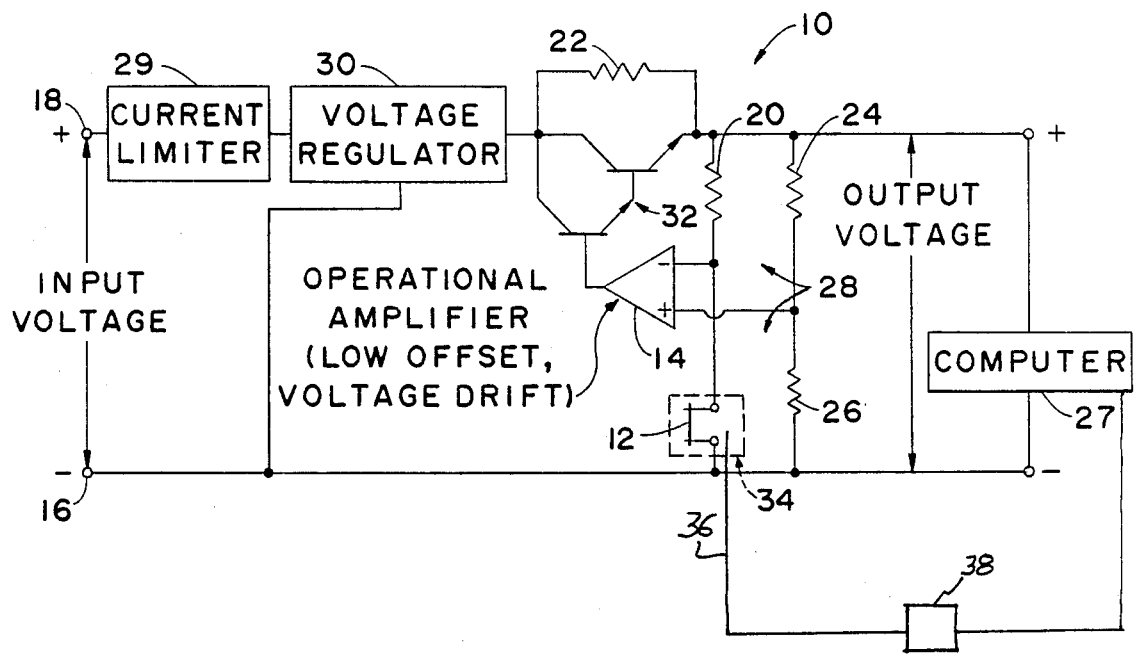

FILAMENT DRIVE CIRCUIT

BACKGROUND OF THE INVENTION pressure equilibrium of two gases, using the difference the thermal conductivity of the two gases, and Particularly to a circuit arrangement that provides appropriate control of the temperature of a heated filament sensor. In addition, the arrangement is free of the influence of changes in ambient temperature and humidity.

The need for accuracy in determining very small amounts of trace gases is discussed in U.S. patent application Ser. Nos. 763,290 and 825,344 by Mark Warchol et al and Warchol, respectively, and also in U.S. Pat. No. 4,454,748 to Terai et al. In the first Warchol et al application, the "Telegas" process and apparatus of U.S. Pat. No. 2,861,450 to Ransley is combined with a device capable of computing the percent of gas content in a molten supply of metal from readings of the thermal conductivity of the content gas and of a carrier gas by a catharometer and from the readings of temperature of the molten supply, all of which is then modified by a conversion factor of the alloy of the molten supply, which is known. Before the Warchol et al disclosure, all of the above readings, measurements, and conversions were done by using temperature charts and alloy tables. The reading of the charts and the arithmetic involved in making the changes often resulted in errors in determining the amount of gas contained in the molten metal. By combining the entire process in the operations of the computing device, these errors were eliminated.

The second of the above Warchol applications eliminates the reference cell employed in the catharometer of the first application, as well as in the Ransley patent, and, inter alia, uses a constant current source in series with the remaining hot-wire sensor. In this manner, the voltage drop across the sensor changes only in response to the precise amount of gas content reaching the sensor. In addition, the elimination of the reference cell eliminated the cumbersome task of providing identical hot-wire sensors needed for accuracy in such systems. As explained in the Warchol application, such sensors are often hand wound, which is tedious and time consuming, and ultimately does not guarantee precise matching of the sensors.

The above Terai et al patent improves the accuracy of the Telegas measurement by isolating the hot-wire sensors from changes in ambient temperature This is effected by disposing the sensors in a housing and then evacuating the interior of the housing. As can be appreciated, evacuating apparatus adds cost and bulk to the instrument, where compactness is needed, as such instruments are often portable devices used on line in casting operations, and cost reductions, as opposed to increases, are sought to meet competition.

In the Ransley system, changing ambient required several readings of partial gas pressures before a stable reading was obtained to provide reasonably accurate indications of the partial pressures. (Partial pressure is the equilibrium Pressure of gas molecules located at a free surface in a body of molten metal in which the gas is dissolved. If the solubility of the gas at a given pressure [e.g., 760 mm of mercury] is known, then a given gas content in the molten metal will give rise to an internal or equilibrium pressure.)

Further, because the reference cell in Ransley was open to the atmosphere, the instrument was subject to error because of changes in humidity. Moisture affects directly the thermal conductivity of the atmosphere such that the hot wire in the reference cell recorded changes in the moisture content of the atmosphere which introduced reading errors.

SUMMARY OF THE INVENTION

The present invention is directed to a highly stable instrument and circuit in which a single heated filament is employed to contact two gases having a substantial difference in thermal conductivity. The circuit and filament are employed in a process of determining the equilibrium of the partial pressure of one gas contained in another gas via changes in natural convective heat transfer caused by differential thermal conductivity of the two gases. More particularly, the instrument includes an active bridge circuit containing the heated filament. Feedback is provided to the bridge circuit to maintain the filament at a constant level of electrical resistance, and hence at a constant temperature. Further, means is provided for supplying the bridge and filament with a highly stable voltage. When a change occurs in the thermal conductivity of the gas mixture, heat transfer from the filament changes, and electrical power supplied to the filament changes accordingly to maintain the filament at constant temperature. This change in electrical power provides a measure of the concentration of one gas in the other. No reference, atmospheric cell is employed such that the present system is not subject to errors resulting of changes occurring in ambient humidity.

BRIEF DESCRIPTION OF THE DRAWINGS

The invention, along with its objectives and advantages, will be best understood from consideration of the following detailed description and the accompanying drawing which is a schematic circuit representation of a preferred embodiment of the invention.

PREFERRED EMBODIMENT

Referring now to the drawing, a circuit 10 is schematically shown in which one end of a hot wire or film sensor 12, hereinafter referred to as "filament" or "heated filament," has one end connected to the negative input terminal of a low thermal drift operational amplifier (op amp) 14. For reasons explained hereinafter, amplifier 14 has a low thermal offset drift characteristic that, in combination with certain other components of circuit 10, provides circuit 10 with highly stable operating characteristics when changes occur in ambient temperature.

Filament 12 can be either a thin wire device, such as a tungsten wire coated with platinum, or a platinum film plated on a substrate such as a thin quartz rod. The resistance of the filament is proportional to the square of the voltage applied to it divided by the area of the filament, the heat transfer coefficient and the difference between filament temperature and ambient temperature. The filament area is constant but ambient temperature and the heat transfer coefficient are variable. The heat transfer coefficient is a function of the composition of the gas, temperature and mode of heat transfer. The system is constructed such that the filament is isolated from flow effects, i.e., forced convection, and in addition, measurements are take with no gas flow through the system. The primary mode of heat transfer with a platinum hot film sensor (limited to a temperature of 400° C. or lower) is therefore natural convection. The thermal conductivity of hydrogen is almost an order of magnitude greater than that of most other gases (except helium and water vapor), which significantly alters the heat transfer coefficient for natural convection. The impact of the other transport properties of hydrogen, in comparison to other gases, on the heat transfer coefficient is negligible.

The other end of filament 12 is connected to the negative terminal 16 of a DC power supply, not otherwise shown in the drawing, except for its positive terminal 18. A low voltage (e.g. 12 v) is preferred, as the system of circuit 10 may be part of a portable instrument used on-line in casting facilities.

A resistor 20 is connected between filament 12 and a common connection between resistors 22 and 24. This arrangement, of course, connects the filament and resistor 20 to the negative input terminal of amplifier 14. The other end of resistor 24 is connected to a resistor 26 and the positive input terminal of amplifier 14. Filament 12 and resistors 20, 24, and 26 provide a bridge circuit 28 in the input of the amplifier. The excitation voltage of bridge circuit 28 is applied to a measuring circuit 27. Circuit 27 can be a digital computing device though analogue devices can be used to measure bridge voltage and compensate for changes in ambient temperature.

Between the positive terminal 18 of the power supply and bridge circuit 28 is connected, in series, a current limiter 29, a voltage regulator 30 and a transistor or a Darlington pair of transistors 32 (as shown). Resistor 22 is connected across the Darlington pair.

Filament 12 is located in a sensor chamber (not shown) in a well known manner that seals the filament from the atmosphere. The chamber, in turn, is mounted in a cavity of a block of metal material 34, indicated only in dash outline in the drawing. Resistor 26, which is parallel to the filament, and resistors 20 and 24 have low temperature coefficients of electrical resistance so that, with changes in ambient temperature, their resistances will not change and thus not affect the electrical and operational characteristics of the filament. Voltage regulator 30 is connected across the power supply, and is a device that provides the bridge circuit and filament with a highly stable voltage for the same reasons.

Current limiter 29 is a device that protects filament 12 against power transients because of the somewhat delicate nature of the filament; the gain provided by amplifier 14 and the Darlington pair 32 is substantial, such that the filament can be destroyed by excessive current flow.

A probe 36 is located in sensor chamber 34 to measure the temperature within the chamber. This probe is connected to a transmitter 38 which supplies a voltage to measuring device 27 that is proportional to the temperature of the chamber. The resolution of this measurement should be ±0.01° C.

The circuit of FIG. 1, as thus far described, works in the following manner. DC power is applied to the components of the circuit from terminals 16 and 18 of a supply of the power. The value of resistor 22 sets the course and major Portion of the current for bridge circuit 28, including filament 12, while the resistance characteristic of the filament itself is such that it is proportioned to the voltage applied as described earlier. The resistances of resistors 20, 24 and 26 are not affected by the voltage applied.

The system is purged by a carrier gas to remove all gases except the carrier gas. The carrier gas is then pumped through the molten metal to be tested for hydrogen. As the gas traverses the molten metal increasing amounts of hydrogen are entrained in the carrier gas until hydrogen partial pressure reaches equilibrium. The mixture of the carrier and hydrogen is carried to the cell of filament 12. The resistance of filament 12 is changed, thereby tending to imbalance bridge 28. Amplifier 14 senses the imbalance in the bridge and increases or decreases the voltage applied to the bridge through the Darlington pair of 32, returning the bridge to a balanced condition by increasing or decreasing the resistance of the filament. The bridge is balanced when the ratio of R24/R26 resistance is the same as R20/filament resistance. If the thermal conductivity of the gas in the sensor chamber of 12 changes, the temperature of heated filament 12 changes, thereby changing its resistance. This change is sensed by amplifier 14 which changes, as per above, the applied voltage to re-balance the bridge, bringing the filament back to its original temperature. The output of the system is therefore the voltage applied to excite the bridge and is a direct measure of gas content in a body of molten metal uncorrected, however, for changes in ambient temperature. The values of the output voltage and sensor temperature are then stored in computing device 27 for comparison to the value representing the carrier gas alone. Sensor temperature is provided to the computer via transmitter 38.

The system of the invention is zeroed by reading the output voltage of bridge 28 and recording ambient temperature with the system purged of all but carrier gas. The zero voltage is adjusted for any difference that may exist between the ambient temperature of this reading compared to the ambient temperature of the reading of equilibrium gas mixture. These readings are generally taken on the order of a minute or less apart so that this correction is minor. The temperature corrected zero voltage is next subtracted from the voltage with the equilibrium gas mixture. This differential voltage is compared to the differential voltage obtained in a similar way with a span gas comprised of a mixture of carrier gas and a known amount of hydrogen and a gas containing zero hydrogen, i.e., a gas comprised of the carrier gas alone. Additionally, differential span voltage is adjusted for the difference between the ambient temperature at the time it was measured and that of the present reading. The span voltage measurement is often done in a laboratory environment, while the present reading is generally taken in the much hotter environment existing in a foundry in the presence of molten metal. Therefore, the correction to the span voltage for ambient temperature may be 4 or 5 percent. The percent of hydrogen in the present measurement is determined by rationing the present differential voltage to the span voltage and multiplying by the Percent of hydrogen in the span gas. This zeroing procedure compensates for long term and thermal drift of amplifier 14 and measuring device 27. The temperature adjustment of the span voltage corrects for the change in heat transfer coefficient attributed to transport property changes in the constituent gases caused by ambient temperature change. This procedure is Preferably performed in measuring device 27.

The system of circuit 10 is different from constant temperature anemometers, which use starting resistors similar to that of 22 in FIG. 1. Anemometers do not, however, employ highly stable voltage supplies, and the starting resistors do not supply the major portion of operating current. These are not needed, as anemometers are employed to measure the velocity of moving fluids in which the changes in heat transfer are more dramatic because the primary mode of heat transfer is forced convection. Publications directed to hot wire and hot film anemometry include TSI Technical Bulletin TB5 (undated) distributed by TSI Inc. of St. Paul, Minn., and a paper entitled "Gas Concentration with Temperature Compensated Aspirating Probe" by Barclay Jones and Randall Wilson, pages 205 to 210 presented at the Symposium on turbulence, Rolla, Mo. 1977, published by Science Press.

Anemometer circuits are not sensitive enough to differentiate heat transfer effects caused by thermal conductivity changes in a natural convection environment. The low volume requirement imposed by the small quantity of hydrogen gas available in a molten metal system makes flow control virtually impossible. Thus hydrogen measurement in the present invention is made with no flow or the sensor is located out of the flow path.

Without the high stability voltage source in the present invention, drift of the voltage supply (e.g. by decay of battery voltage during use) would cause drift in the output voltage. In an anemometer, this drift would not be significant compared to the voltage at full scale flow. Because of the much smaller differential between zero and full scale output in the present invention, drift associated with the source voltage can cause errors of 10% or greater.

In an anemometer, the filament current may change by 100% over the range of zero to full scale velocity of gas flow. In the system of the present invention the filament current changes by only a few percent over the range of hydrogen partial pressures extant in most molten aluminum alloy melts. Without resistor 22, the circuit of FIG. 1 can have two stable modes. The first mode is zero current through the bridge (with no positive offset at the output of amplifier 14). This mode is trivial and useless for measuring purposes. The other stable mode exists when current flows through the bridge controlled by amplifier 14, as described earlier. In an anemometer, resistor 22 is employed only to create a small imbalance to assure that the circuit does not operate in the trivial mode. Once started, resistor 22 is unnecessary in an anemometer. In the present invention, the current through the Darlington pair 32 is made as small as practicable by supplying the major portion of the current through the starting resistor 22. Because the current gain of transistors is generally inversely proportional to the current, this maximizes the gain of the system. These differences from anemometer practice maximize the stability and sensitivity of the present invention.

While the invention has been described in terms of preferred embodiments, the claims appended hereto are intended to encompass all embodiments which fall within the spirit and scope of the invention.

What is claimed is:

1. A method of determining the amount of a gas dissolved in a molten metal using a carrier gas circulated in the molten metal to entrain and carry the dissolved gas in a closed path to a filament that is sensitive to changes in the thermal conductivities of gases when the filament is exposed to the gases, the two gases having different thermal conductivities, and the filament being connected as one leg of a bridge circuit, the method comprising:

heating said filament to a temperature range in which the electrical resistance of the filament changes when the thermal conductivity of a mixture of the carrier gas and dissolved gas changes, transferring the heat of the filament to said gases by natural convection, the electrical resistance of the filament changing in response to a change in temperature caused by a change in the thermal conductivity of the gas mixture, and restoring the resistance of the filament to an original value in response to the change in filament temperature by changing the voltage supplied to the bridge circuit, the change in voltage being a measurement of the amount of gas dissolved in the molten metal.

2. Apparatus for determining the content of a gas dissolved in a molten metal, said apparatus including a bridge circuit in which a filament for sensing the thermal conductivities of gases directed to the filament via a closed path is connected as one leg of the circuit, and in which a power supply is connected to supply current to the filament to heat the same to a temperature range in which the electrical resistance of the filament changes when the thermal conductivity of a mixture of gases reaching the filament changes, the electrical resistance of the filament changing in response to changes in its temperature caused by changes in gas thermal conductivity produced in a carrier gas by the dissolved gas, the improvement comprising:

a voltage regulator connected across the power supply to provide the power supply with a highly stable output voltage, and a circuit arrangement connected between the bridge circuit and voltage regulator that is effective to restore the resistance of the filament to an original value in response to said change of filament temperature by changing the voltage supplied to the bridge circuit, said change in voltage being a measurement of the amount of gas dissolved in the molten metal.

* * * * *

UNITED STATES PATENT AND TRADEMARK OFFICE
CERTIFICATE OF CORRECTION

PATENT NO. : 4,829,810

DATED : May 16, 1989

INVENTOR(S) : Daniel A. Anderson et al

It is certified that error appears in the above-identified patent and that said Letters Patent is hereby corrected as shown below:

Col. 1, line 5    Insert "The invention relates generally to the measurement of partial" before --pressure--.

Col. 1, line 6    Insert "in" before --the-- (first occurrence).

Col. 1, line 7    Change "Particularly" to --particularly--.

Col. 1, line 61    Change "Pressure" to --pressure--.

Col. 2, line 66    Change "take" to --taken--.

Col. 3, line 61    Change "Portion" to --portion--.

Col. 4, line 54    Change "rationing" to --ratioing--.

Col. 4, line 55    Change "Percent" to --percent--.

Col. 4, line 62    Change "Preferably" to --preferably--.

Signed and Sealed this

Nineteenth Day of September, 1989

Attest:

DONALD J. QUIGG

Attesting Officer

Commissioner of Patents and Trademarks